(12) United States Patent
Dixon et al.

(10) Patent No.: US 9,040,080 B2
(45) Date of Patent: May 26, 2015

(54) PROCESSING OF HEAT-SENSITIVE ACTIVE AGENTS

(75) Inventors: Hong Dixon, Helotes, TX (US); Joseph A McDonough, Helotes, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 1128 days.

(21) Appl. No.: 12/255,447

(22) Filed: Oct. 21, 2008

(65) Prior Publication Data

US 2010/0098754 A1  Apr. 22, 2010

(51) Int. Cl.
*A61J 3/07*  (2006.01)
*A61K 9/48*  (2006.01)
*A61K 9/50*  (2006.01)
*A61K 9/16*  (2006.01)
*A61K 9/70*  (2006.01)

(52) U.S. Cl.
CPC ............... *A61J 3/07* (2013.01); *A61K 9/1647* (2013.01); *A61K 9/70* (2013.01)

(58) Field of Classification Search
CPC .............. C08L 2207/53; A61K 2039/55555; A61K 49/0093; A61K 9/5153; B82Y 5/00; B82Y 30/00; B29C 47/0066; B29C 47/004; A61B 2017/00004; D01D 5/003; D01D 5/34; D01D 10/02; D01D 5/00; D01F 6/625

USPC .......... 424/405, 408, 409, 499, 500, 501, 490, 424/493, 497, 451; 428/402–402.24, 407, 428/403, 423.1, 474.4; 423/338; 264/53, 264/41, 4–4.7; 427/89.9, 213.3–213.36; 521/57, 56, 76, 142

See application file for complete search history.

(56) References Cited

U.S. PATENT DOCUMENTS

| | | | | |
|---|---|---|---|---|
| 5,629,077 | A | * | 5/1997 | Turnlund et al. ............ 623/1.15 |
| 5,718,921 | A | * | 2/1998 | Mathiowitz et al. ......... 424/497 |
| 5,993,374 | A | * | 11/1999 | Kick ............................... 600/8 |
| 6,500,463 | B1 | | 12/2002 | Van Lengerich |
| 2004/0176341 | A1 | * | 9/2004 | Chou et al. .................... 514/179 |
| 2007/0003753 | A1 | * | 1/2007 | Asgari ........................ 428/315.5 |
| 2007/0134411 | A1 | * | 6/2007 | Cont et al. ............... 427/213.34 |

* cited by examiner

*Primary Examiner* — James J Seidleck
*Assistant Examiner* — S. Camilla Pourbohloul
(74) *Attorney, Agent, or Firm* — Grossman, Tucker et al

(57) ABSTRACT

The present disclosure relates to a method of melt processing an active agent. The method may include encapsulating an active agent in a first polymer material exhibiting a first processing temperature $T_1$ and forming capsules including the active agent. The method may also include melt processing the capsules with a second polymer material exhibiting a second processing temperature $T_2$, wherein $T_1 > T_2$.

16 Claims, 3 Drawing Sheets

PROCESSING OF HEAT-SENSITIVE ACTIVE AGENTS

FIELD OF THE INVENTION

The present disclosure relates generally to processing heat sensitive active agents and, in particular, the use of a first polymer having a relatively higher melt processing temperature for encapsulation of an active agent, which may then be combined with a second polymer having a relatively lower melt processing temperature. The encapsulated active ingredient may then be melt processed without release of the active ingredient and/or without significant active ingredient degradation.

BACKGROUND

In certain circumstances, it may be desirable to regulate the release of an active agent, such as a pharmaceutical compound or food additive, by a controlled release mechanism. Controlled release of an active agent may be facilitated by the use of biodegradable devices, which may slowly degrade in or upon contact with the body and release a given portion of the active agent from the device. Such controlled release devices may include capsules, tubes, fibers, films or tablets and may be produced using melt processing technologies such as injection molding or extrusion, where the active agent may be encapsulated in the device. However, some active agents may undergo a degree of degradation during thermal processing as the active agent may exhibit a degradation temperature that is lower than the temperatures necessitated by processing. The agent may then be less effective.

SUMMARY OF THE INVENTION

An aspect of the present disclosure relates to a method of melt processing an active agent. The method may include encapsulating an active agent in a first polymer material exhibiting a first processing temperature $T_1$ and forming capsules including the active agent. The method may also include melt processing the capsules with a second polymer material exhibiting a second processing temperature $T_2$, wherein $T_1 > T_2$.

Another aspect of the present disclosure relates to a method of forming a controlled release material. The method may include forming first mixture of an active agent, a first polymer material and a first solvent $S_1$, wherein the first polymer material exhibits a first processing temperature $T_1$. The method may also include forming a second mixture including a dispersed phase of the first mixture in a second solvent $S_2$. The first solvent $S_1$ may be removed from the second mixture and capsules may be formed including the active agent. The capsules may then be melt processed with a second polymer material exhibiting a processing temperature $T_2$, forming a controlled release material, wherein $T_1 > T_2$.

A further aspect of the present disclosure relates to a method of forming a controlled release material. The method may include forming a first mixture of an active agent, a first polymer material and a first solvent $S_1$, wherein the first polymer material exhibits a first processing temperature $T_1$. The method may also include forming a second mixture including a dispersed phase of the first mixture in a second solvent $S_2$ and removing the first solvent $S_1$ from the second mixture and forming capsules including the active agent. The capsules may then be incorporated in a second inorganic biodegradable material.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein.

DETAILED DESCRIPTION

Figure 2:
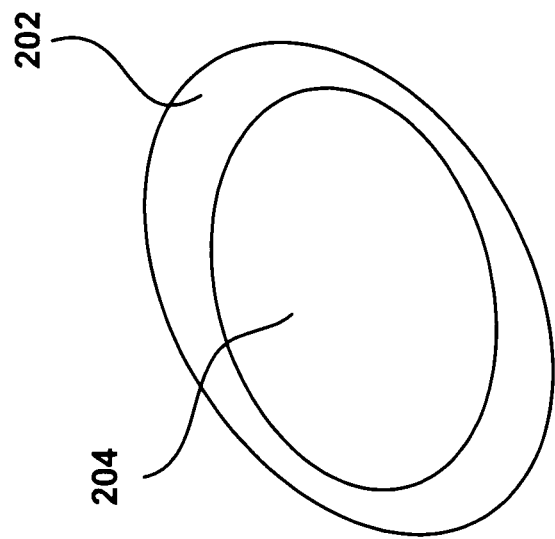
FIG. 2 illustrates an example of a microcapsule including an active agent surrounded by a shell of a first polymer.

The present disclosure relates to processing active agents and, in particular, relates to the use of a first polymer having a relatively high processing temperature $T_1$ in combination with a second polymer having a relatively low processing temperature $T_2$. The first polymer may be used for encapsulating active agents that may be sensitive to elevated temperatures. Active agents may include pharmaceutical active ingredients such as herbs, vitamins, or other natural or synthetic chemical substances utilized in the treatment, prevention, cure or diagnosis of disease or to enhance physical or mental well being. In addition, active agents may include food ingredients such as flavor enhancers, as well as chemical agents for various chemical applications. Heat sensitivity of the active agents may be understood herein as the potential of the active agent to degrade or exhibit a loss in activity, physical properties or other characteristics upon exposure to heat or stress over a given period of time.

More specifically, the active agents herein may include pharmaceutical active agents such as carbonic anhydrase inhibitors, which may be understood as a group of diuretic medications which act to inhibit the enzyme carbonic anhydrase to create a metabolic acidosis. Many of these medications are used in the treatment of glaucoma. One example is brinzolamide, which is otherwise known as (R)-(+)-4-Ethylamino-2-(3-methoxypropyl)-3,4-dihydro-2H-thieno[3,2-e]-1,2-thiazine-6-sulfonamide-1,1-dioxide. Brinzolamide has the empirical formula $C_{12}H_{21}N_3O_5S_3$. The pharmaceutical active agents may also include osteoporetics (i.e. drugs that influence bone metabolization), estrogen uptake inhibitors, hypolipodemic agents such as statins, hormones, prostoglandins and associated derivatives, anti-psychotic drugs and anti-inflammatories.

Active agents have been encapsulated by direct melt processing, without regard to the processing temperature of the encapsulating agent, wherein the active agent may be encapsulated by methods including injection molding, blow molding or extrusion of the active agent in a polymer. However, under these circumstances, the active agents have been found to degrade during processing, which, as alluded to above, may reduce the effectiveness of the agent, such as by reducing the agent's mechanical properties or physiological effectiveness. Direct melt processing may be understood as encapsulating or otherwise processing an active agent via a melt processing technique, such as injection molding, blow molding or extrusion, without exposing the active agent to a prior encapsulation step. It may be appreciated that degradation of the active agent may be caused by exposure of the active agent to temperature or shear profiles dictated by the encapsulating polymer composition, which may exhibit a processing temperature window that exceeds the degradation temperature of the active agent.

For example, about 5% drug degradation was found when brinzolamide, having a melting point in the range of 130-131° C. was directly melt processed by extrusion with poly(lactic acid-co glycolic acid) at 75:25 and 85:15 molar ratios. Melt processing temperatures of the poly(lactic-co glycolic acid) were in the range of 140° C.-160° C. This is significantly greater than the melting point of the brinzolamide. Thus, the brinzolamide, when exposed to temperatures significantly higher than its melting point, and beyond its associated degradation temperature, will cause the brinzolamide to partially and/or fully degrade.

The processing of the active agents herein, by contrast to the above, includes, for example, dual stage processing, where the active agent may be encapsulated via a first stage procedure utilizing relatively low processing temperatures, followed by a second stage performed at relatively higher processing temperatures. During the first stage a first polymer material exhibiting relatively high processing temperature $T_1$ may be used to encapsulate the active agent. It has been found that under these circumstances, the encapsulated active agent may withstand relatively higher processing temperatures, which are realized in a second stage melt processing procedure.

In other words, the first polymer may exhibit a processing temperature $T_1$ that is greater than the processing temperature of the second polymer material $T_2$, i.e., $T_1 > T_2$. It may be appreciated then that the first polymer, may also exhibit a relatively higher processing temperature $T_1$ than the degradation temperature $T_3$ of the active agent, wherein $T_1 > T_3$. Processing temperature may be understood as a temperature of a polymer material that provides sufficient flow for the polymer material to be processed or shaped by a melt processing technique (extrusion, injection molding, compression molding, thermoforming, etc.). In some situations this may amount to what is typically referred to as the polymer melting temperature or Tm, which may apply in those situations where the polymer utilized is crystalline or has relatively high crystallinity (e.g. greater than or equal to 50 weight percent). In other situations the processing temperature may be a temperature that is above what is typically referred to as the glass transition temperature or Tg, which may apply in those situations where the polymer utilized is amorphous or has relatively high amorphous content (e.g. greater than or equal to 50 weight percent). The processing temperature may also change depending on the process and/or the shear stress provided during processing. Degradation temperature $T_3$ may be understood as that temperature point which results in reduced activity (physiological effectiveness). This reduction in effectiveness may be due to breaking of one or more covalent bonds in the active agent and an associated change in its chemical characteristics (e.g. a change in chemical structure, active agent molecular weight, active agent acid or base functionality). Degradation temperature may also result in other modifications in the chemical activity that may not necessarily be attributed to the breaking of a covalent bond. For example, degradation may occur at a temperature that contemplates e.g., the modification of a salt to a free acid or base (such as the loss of hydrochloric acid from an amine-hydrochloric acid salt) and/or dehydration and/or desolvation (e.g. loss of water or solvent from a hydrate crystal form of a given active agent). An example of the latter would be heating of a hydrate such $CaSO_4.2H_2O$ along with the release of water.

Furthermore, the processing temperature of the second polymer material may be greater than, less than or the same as the degradation temperature of the active agent. In one example, the processing temperature of the second polymer material may be less than the degradation temperature of the active agent, wherein $T_2 < T_3$. In another example, the processing temperature of the second polymer material may be greater than the degradation temperature of the active agent, wherein $T_3 < T_2$. However, as the active agent is encapsulated in the first polymer, which has a processing temperature greater than the processing temperature of the second polymer, active agent degradation may be reduced or non-existent.

The first processing stage, which is used for encapsulation, may include a relatively low temperature process. A relatively low temperature process may be understood as a process that exhibits processing temperatures that are less than the degradation temperature of the active agent. For example, encapsulation of the active agent may occur by one of various encapsulation techniques such as emulsion polymerization, coacervation, or emulsion-solvent evaporation encapsulation.

In one example emulsion-solvent evaporation may be used and the process may begin by forming a first mixture of a first polymer or polymer precursor having a relatively high processing temperature $T_1$ in a first solvent $S_1$, which may dissolve at least a portion of the first polymer. The polymer or polymer precursor may be added to the solvent at approximately 1% to 20% by volume, including all values and ratios therein, such as 5% to 10% by volume. In addition, an active agent may be added to the first mixture either prior to or after the addition of the first polymer material. The active agent may be present in the range of 10% to 60% by weight of the first polymer material, including all values and increments therein, such as 20% to 40% by weight.

The first mixture may then be added to a second solvent $S_2$ forming a second mixture, wherein the second solvent $S_2$ and first solvent $S_1$ may be characterized as being immiscible. For example, the first solvent $S_1$ and second solvent $S_2$ may be selected such that they have a Hildebrand solubility parameter values ($\delta$) that are greater than +/−2.0 units of one another, as measured in $(MPa)^{1/2}$. Accordingly, the solvents may be selected such that the difference in solubility parameters between them may be greater than, e.g. +/−3.0 units of one another, or greater than +/−4.0 units of one another, or greater than 5.0 units of one another, etc. Those skilled in the art may appreciate that the Hildebrand solubility parameter represents the square root of the cohesive energy density and provides a numerical estimate of the degree of interaction of selected materials. The first solvent may be present in the second solvent in the range of 5% to 20% by weight of the second solvent, including all values and increments therein.

The first mixture may be dispersed as a discontinuous phase in the second solvent $S_2$, which may be facilitated by mixing. In addition, a surfactant may be added to the second mixture prior to or after the addition of the first mixture. At least a portion of the first solvent $S_1$ may then be removed from the second mixture and capsules including the first polymer and active agent may be formed. The capsules may be removed from the second mixture and washed in a third solvent. In addition, the capsules may be dried. Drying may be facilitated by the application of heat and/or a change in vapor pressure, such as by a vacuum oven.

Figure 1:
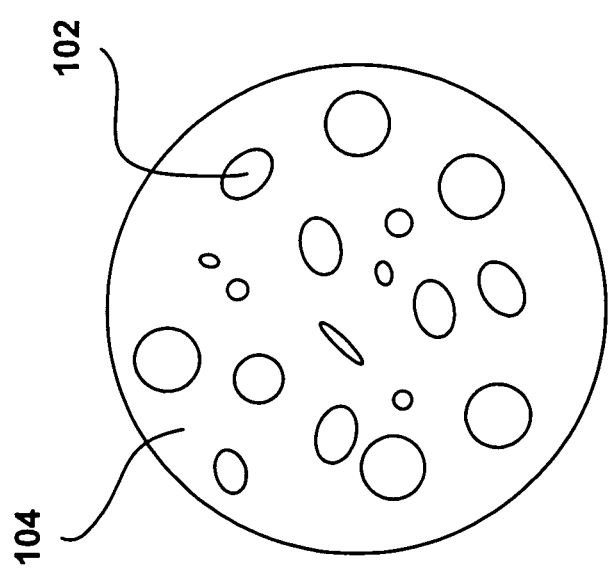
FIG. 1 illustrates an example of a microcapsule including domains of an active agent within a first polymer material matrix.

In one example, the encapsulated agent may be dispersed throughout a matrix of the first polymer. As illustrated in FIG. 1, the active agent 102 may form domains in a matrix of the first polymer 104. In one example, the domains may be discrete. In other embodiments, such as the example illustrated in FIG. 2, the first polymer may form a shell or coating 202 around the active agent 204. In addition, the domains may be relatively uniform in size within +/−5% of the average diameter (largest linear dimension); or in some examples, the domains may be relatively non-uniform. The capsules may be microcapsules having a diameter in the range of 0.01 μm to 1 mm, including all values and increments therein at 0.01 μm increments, such as in the range of 0.1 μm to 10 μm. The active agent may be present in the capsules in a range of 10% to 60% by weight, including all values and increments therein, of the active agent and first polymer.

In addition, the active agent domain 102 may be sourced from particulate, i.e. nanoparticulate which may be understood as particles having a largest linear dimension (e.g. a diameter) of less than or equal to 500 nanometers. In such manner, the present disclosure provides a method for encapsulating a nanoparticulate active ingredient in a polymer material that has a first processing temperature $T_1$ and melt processing said encapsulated nanoparticulate with a second polymer material exhibiting a second melt processing temperature $T_2$, wherein $T_1 > T_2$.

The resulting encapsulated agent may then be processed by a second melt processing technique with a second polymer having a relatively lower processing temperature $T_2$. The thermal, melt processing technique may include techniques such as injection molding, blow molding, extrusion, twin screw extrusion, compression molding, transfer molding, etc. to form tablets, capsules, micro-capsules or nano-capsules as well as fibers, films, rods, pellets and/or other devices. The active agent may be present in the range of 1% to 50% by weight, including all values and increments therein, in the final product, which as noted, contains the active agent, the first polymer and the second polymer. Optionally, other excipients may be added during the first stage or second stage of the forming process.

The active ingredient may exhibit degradation of less than or equal to 2.0% by weight, including all values and increments therein, such as in the range of 0% to 1.0% by weight of the active ingredient. Degradation may be determined by HPLC, wherein degraded active ingredient may exhibit a different (typically lower) molecular weight as compared to the active ingredient as provided.

As alluded to above, the active agents may include pharmaceutical ingredients such as herbs, vitamins, or other chemical substances utilized in the treatment, prevention, cure or diagnosis of disease or to enhance physical or mental well being. In addition, active agents may include food ingredients such as flavor enhancers, as well as chemical agents for various chemical applications. Furthermore, active agents may include chemical agents that may be utilized in various applications, such as adhesives, cosmetics, perfumes, pesticides, herbicides, textiles, and/or indicators. The active agents may exhibit a degradation temperature of less than 200° C., including all values and increments in the range of 35° C. to 200° C., such as in the ranges of 50° C. to 150° C., 100° C. to 160° C., 120° C. to 140° C., etc.

In one example, the active agent may include inhibitors, which may be understood as a substance that may stop or hinder a chemical reaction. Inhibitors may include, for example an enzyme inhibitor, which may be understood as a molecule that may bind to an enzyme, which may result in decreased activity of the enzyme. Enzyme inhibitors may be natural or synthetic. Brinzolamide may be an exemplary carbonic anhydrase inhibitor and may be used for treating ocular hypertension, which as alluded to above may have a degradation temperature in the range of 120° C. to 140° C. including all values and increments therein, such as in the range of 130° C.-131° C.

The first polymer may include a biodegradable polymer and/or a biocompatible polymer material. Biodegradable may be understood as the ability of the polymer material to breakdown by, for example, enzymes produced by living organisms, in the presence of oxygen, or the presence of water. Biocompatible may be understood as the quality of having relatively non-toxic or non-injurious effects on biological systems. The first polymer may form a first controlled release membrane and/or barrier to protect the active agent from degradation due to heat exposure and/or exposure to the environment, including exposure to moisture, sunlight or other materials. The polymer material may include, but is not limited to polyesters such as poly(lactic acid) and its copolymers including poly(lactic co-glycolic acid), poly(glycolic acid), polycarbonates, poly(orthoesters), polyamides, poly(esteramides), polyurethanes, polyanhydrides, polyphosphazenes, polyhydroxyalkanoate, etc. In addition, the first polymer may include starch-based polymers and chitosan. In addition, the first polymer may exhibit a processing temperature $T_1$ in the range of 150° C. to 400° C. In one example, the first polymer may be at least partially soluble in a first solvent $S_1$, discussed herein.

The second polymer may provide additional barrier protection exhibiting a second set of barrier properties and/or further regulate release of the active agent or provide other properties to the encapsulated active agent. The second material may include, any of the polymers noted above for the first polymer, provided, as noted that the second polymer has a processing temperature that is lower than the first polymer. The second polymer material may specifically include a poly(caprolactone) as well as other types of polyester polymers. The second polymer may exhibit a processing temperature $T_2$ of less than 200° C., including all values and increments in the range of 50° C. to 200° C., 100° C. to 160° C., etc.

It may also be appreciated that in another example, the capsules including the active agent and first polymer material may be incorporated in a second non-polymeric medium, such as an inorganic biodegradable material such as calcium phosphate or layered double hydroxides.

The first solvent $S_1$ may include an organic solvent, such as, for example, an aliphatic or aromatic hydrocarbon, having in the range of 3 to 20 carbons, including all values and increments therein, such as cyclohexane, hexane, dichloromethane, tetrahydrofuran, ethyl acetate, chloroform, hexafluoroisopropanol or acetone. The second solvent $S_2$ may be hydrocarbon based, including hydrocarbon based alkane solvents, having in the range of 5 to 50 carbons, including all values and increments therein. In one example, the second solvent $S_2$ may include mineral oil, such as parrafinic oil, napthenic oil or aromatic oil. The second solvent $S_2$ may also include organic lipids, including waxes, fats or other oils, as well a silicones, including silicone oils or grease. The third solvent $S_3$ may include a relatively inert organic solvent such as an aliphatic hydrocarbon having in the range of 3-20 carbons, including hexane, etc. It may be appreciated that the first solvent $S_1$ and third solvent $S_3$ may be relatively similar or the same in a given process.

As noted above, excipients may be employed in either the first mixture or the second mixture or during a post encapsulation step. Examples of excipients may include flavorants, colorants, binders, coatings, disintegrants, fillers, diluents, preservatives, sorbents, sweeteners, pore forming materials including poly(ethylene glycols) or surfactants, neutralizers including salt of zinc acetate, etc. The excipients may be in liquid, powder or particle form and may be present in the range of 10% to 1,000% of the weight of the active agent, including all values and increments therein. It may be appreciated that the excipient may be relatively inert as compared to the active ingredient, aiding, for example, in the administration, flavor, or solubility of the encapsulating material.

Surfactants may also be employed in either the first solvent or second solvent, to regulate droplet size diameter and droplet size distribution, or stabilize capsule suspensions after formation. One surfactant that may be employed is sorbitan monooleate, which may generally be available as a mixture of partial esters of sorbitol and its mono- and dianhydrides with oleic acid. It is also contemplated herein that one may employ those surfactants that have relatively low HLB values (i.e. hydrophilic-lipophile balance). HLB value is reference to an indication of the relative solubility of the surfactant. That is, the lower the HLB value the more lipophilic or oil soluble and the higher the HLB value the more water soluble or hydrophilic surfactant is present. HLB values may generally fall within the range of 0.5 to 19.5. Therefore, HLB values, such as less than or equal to 10.0, may be employed herein. Examples of surfactants may include Span 80 or Tween 20.

It may therefore be appreciated that the present disclosure provides the ability to encapsulate an active agent, in a first polymer material having a first processing temperature ($T_1$), which is then dispersed in a second polymer material having a processing temperature $T_2$, wherein $T_1$ is greater than $T_2$. The first polymer is configured to encapsulate the active agent without the use of a melt processing technique.

Figure 3:
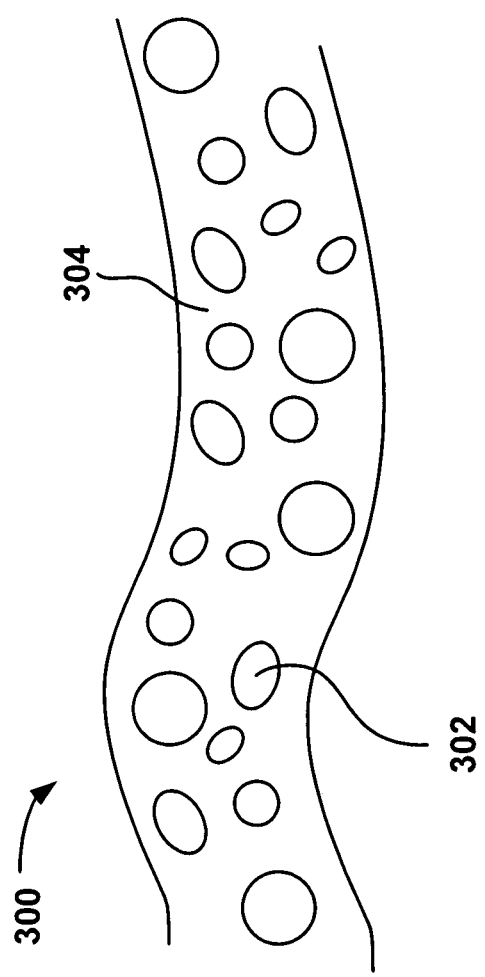
FIG. 3 illustrates an example of a product including an active agent encapsulated in a first polymer material dispersed within a second polymer material.

This therefore provides the unique ability to melt process the encapsulated active agent without substantially degrading the active agent. This may be due to the feature that the first polymer material may serve to protect the active agent, from the elevated temperatures that are utilized to melt processing of the second polymer. In this manner, melt processing of an encapsulated active agent may take place at temperatures not previously considered available for active agent melt processing. In addition, in this manner, melt processing of the active agent may take place where the amount of degradation of the active agent is significantly reduced and the levels of active agent that may be delivered are significantly enhanced. Products that may be provided herein include controlled release materials such as films, fibers, tubing, that may all be melt processed to a desired configuration. As illustrated in FIG. 3, an example of a product 300 may include an active agent encapsulated in a first polymer 302 dispersed within a matrix of a second polymer 304 assuming the shape of a fiber.

EXAMPLES

It may be appreciated that the examples herein are presented for purposes of illustration only and are not meant to limit the scope of the present disclosure.

The active ingredient brinzolamide was microencapsulated in two poly(lactic acid-co-glycolic acid) (PLGA) copolymers, one having a molar ratio of 75/25 (PLGA7525) and one having a molar ratio of 85/15 (PLGA 8515) as discussed further below. The theoretical amount of active agent was 40% by weight in each microencapsulation formulation. The two microsphere formulations were extruded with a lower melting point polymer, poly(caprolactone) (CAPA686), wherein the microspheres were present at 40% by weight and the poly(caprolactone) was present at 60% by weight, forming fibers incorporating the microcapsules therein. HPLC analysis demonstrated that there was an absence of thermal degradation of the brinzolamide in the fibers.

Example 1

Formulation of Brinzolamide in a (PLGA) with a Molar Ratio of 75/25

A solution of 8% PLA-PGA having a 75/25 molar ratio in acetone was prepared with 1 gram of brinzolamide. The solution was stirred in 170 grams of mineral oil with 4% Span80 in a beaker. After the solvent was allowed to evaporate completely, the resulting microspheres were repeatedly washed in hexane and then dried in a vacuum oven. A mixture of the prepared microspheres and poly(caprolactone) at a ratio of 2:3 by weight was extruded in a lab scale twin-screw extruder (Thermo HAAKE MiniLab) at about 75° C. forming fibers.

Example 2

Formulation of Brinzolamide in a (PLGA) with a Molar Ratio of 85/15

A solution of 8% PLA-PGA having an 85/15 molar ratio in acetone was prepared with 1 gram of brinzolamide. The solution was stirred in 170 grams of mineral oil with 4% Span80 in a beaker. After the solvent was allowed to evaporate completely, the resulting microspheres were repeatedly washed in hexane and then dried in a vacuum oven. A mixture of the prepared microspheres and poly(caprolactone) at a ratio of 2:3 by weight was extruded in a lab scale twin-screw extruder (Thermo HAAKE MiniLab) at about 75° C. forming fibers.

Example 3

The payload of the two formulations of Example 1 and Example 2 as microcapsules and fibers were examined. Microsphere and fiber samples, 10 to 20 mg each, were dissolved in 2 mL of methylene chloride. The dissolved samples were then added to 50 mL of pH 5.0 phosphate buffered saline solutions. The amount of brinzolamide in the aqueous solution was analyzed by HPLC (High Performance Liquid Chromatography). Table 1 summarizes the results of the tests.

TABLE 1

| | Actual Payload (%) | |
| --- | --- | --- |
| Sample | Composition | Actual Payload (%) |
| Example 1 Microspheres | 40% brinzolamide 60% PLGA 75/25 molar ratio | 28.7 ± 6.0 |
| Example 2 Microspheres | 40% brinzolamide 60% PLGA 85/15 molar ratio | 30.3 ± 10.2 |
| Example 1 Fibers | 40% brinzolamide and PLGA 75/25 molar ratio 60% poly(caprolactone) | 10.1 ± 1.1 |
| Example 2 Fibers | 40% brinzolamide and PLGA 85/15 molar ratio 60% poly(caprolactone) | 10.7 ± 2.6 |

Example 4

Figure 4:
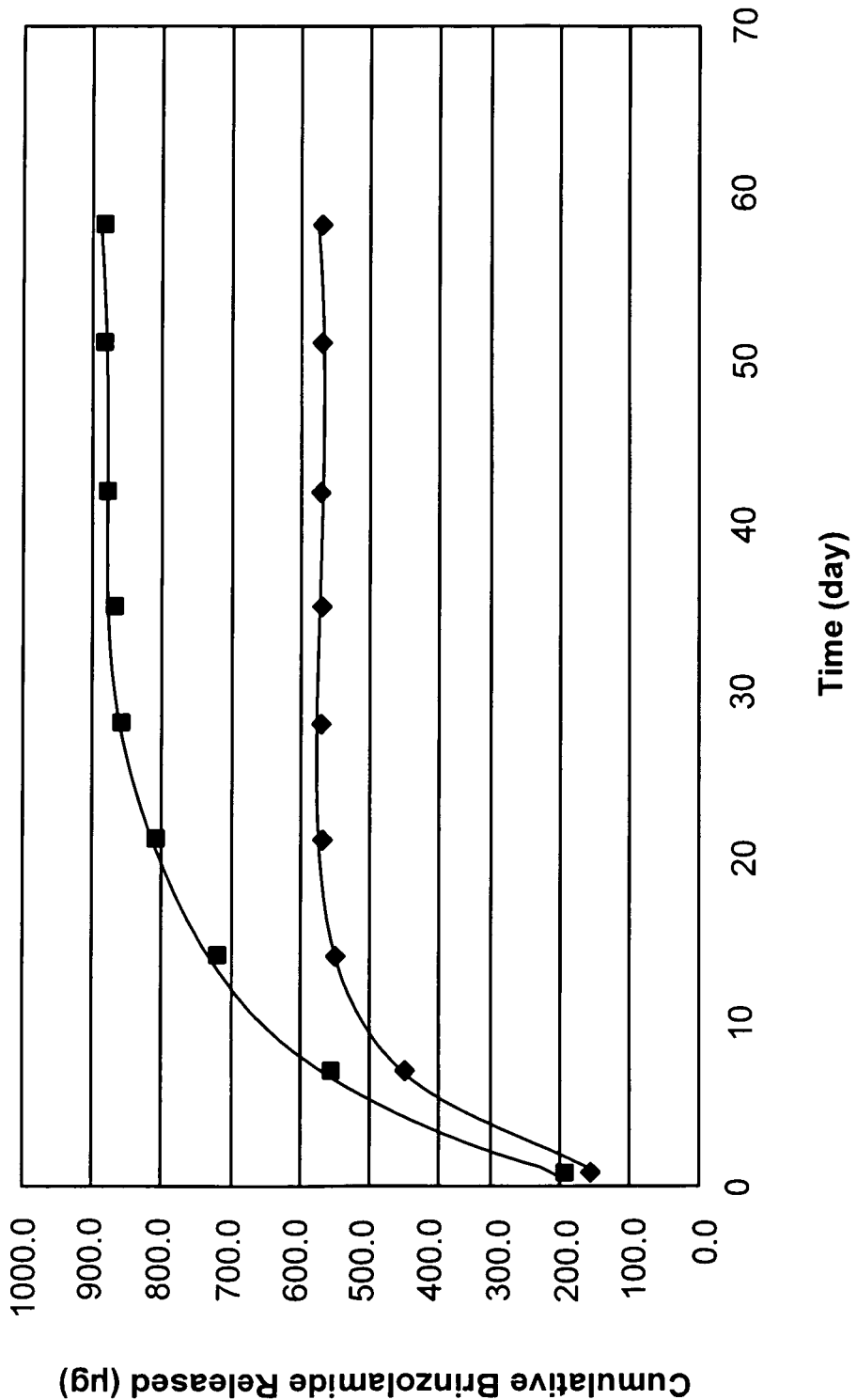
FIG. 4 illustrates an example of cumulative brinzolamide release over a period of time.

In addition to determining the payload of the microcapsules and fibers, the in vitro release of the extruded fibers of Example 1 and Example 2 were examined. Sections of the extruded fibers with diameters in the range of 0.3 to 0.6 mm were cut into 15 mm length. Each length was placed in 5 mL of pH 7.4 phosphate buffered saline release media and put in a 37° C. shaker bath. Four specimens per formulation were studied over a 58 day period. The release media was analyzed and completely replaced weekly. FIG. 4 illustrates the cumulative release of brinzolamide over the 58 day period. The average daily release rate and number of weeks of sustained drug release are illustrated in Table 2 below.

TABLE 2

Average Daily Release Rate

| Sample | Theoretical Composition | Average Daily Release of Brinzolamide (μg/day) | Number of weeks Sustained Release (wk) |
|---|---|---|---|
| Example 1 Fiber | 16% brinzolamide 24% PLGA 75/25 molar ratio 60% poly(caprolactone) | 38.5 | 2 |
| Example 2 Fiber | 16% brinzolamide 24% PLGA 85/15 molar ratio 60% poly(caprolactone) | 30.6 | 4 |

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

The invention claimed is:

1. A method of melt processing an active agent comprising:
   forming a first mixture of an active agent, a first polymer material and a first solvent $S_1$, wherein said first solvent comprises an organic solvent and said first polymer is present in said first solvent at 1% to 20% by volume and said active agent is a nanoparticulate having a largest linear dimension of less than or equal to 500 nanometers and a degradation temperature of less than 200° C.;
   adding said first mixture to a second solvent and forming a second mixture including a dispersed phase of said first mixture in said second solvent, wherein said second solvent comprises a hydrocarbon;
   removing said first solvent from said second mixture;
   encapsulating said active agent in said first polymer material exhibiting a first processing temperature $T_1$, wherein said active agent forms domains within a matrix of said first polymer, wherein said domains are discrete, and forming a plurality of capsules including said active agent; and
   melt processing said capsules with a second polymer material by injection molding, blow molding, extrusion, twin screw extrusion, compression molding, or transfer molding, wherein said second polymer exhibits a second processing temperature $T_2$, wherein $T_1>T_2$, wherein said plurality of capsules are dispersed within a matrix of said second polymer and wherein said encapsulating of said active agent in the first polymer is conducted at a relatively lower temperature than said melt processing with said second polymer; and
   wherein said first polymer exhibits a processing temperature $T_1$ in the range of 120° C. to 400° C., and said second polymer exhibits a processing temperature $T_2$ in the range of less than 200° C.

2. The method of claim 1, wherein said active agent exhibits less than 2% by weight degradation after melt processing.

3. The method of claim 1, wherein said first solvent $S_1$ and second solvent $S_2$ have Hildebrand solubility parameter values, and said solubility parameter values have a difference that is greater than 2.0 units of one another as measured in $(MPa)^{1/2}$.

4. The method of claim 1, wherein said active agent is a carbonic anhydrase inhibitor.

5. The method of claim 4 wherein said carbonic anhydrase inhibitor comprises brinzolamide.

6. The method of claim 1 wherein said active agent comprises a pharmaceutical active agent.

7. The method of claim 1 wherein said active agent is selected from the group consisting of osteoporetics, estrogen uptake inhibitors, hypolipodemic agents, hormones, protoglandins and derivatives, anti-psychotic drugs and anti-inflammatories.

8. The method of claim 1, wherein said first polymer exhibits a processing temperature $T_1$ in the range of 120° C. to 400° C., and said second polymer exhibits a processing temperature $T_2$ in the range of less than 200° C.

9. The method of claim 1, wherein said active agent is present in said capsules in the range of 10% to 60% by weight.

10. The method of claim 1, wherein said capsules have an average diameter in the range of 0.01 μm to 100 μm, including all values and increments therein.

11. The method of claim 1, wherein said active agent exhibits a degradation temperature $T_3$ of less than 200° C. and $T_1>T_3$.

12. The method of claim 1 wherein said melt processing of said capsules with a second polymer comprises forming fibers, films, rods, or pellets.

13. The method of claim 1 wherein said active agent comprises a food ingredient.

14. The method of claim 1 wherein said first polymer comprises a biodegradable polymer.

15. The method of claim 1 wherein said first polymer comprises a biocompatible polymer.

16. The method of claim 1 wherein said first polymer is selected from poly(lactic acid) and its copolymers, polycarbonates, poly(orthoesters), polyamides, poly(esteramides), polyurethanes, polyanhydrides, polyphosphazenes, polyhydroxyalkanoate, starch-based polymers or chitosan.

* * * * *